US012678340B2

(12) United States Patent
Sablone

(10) Patent No.: US 12,678,340 B2
(45) Date of Patent: Jul. 14, 2026

(54) METHOD FOR PRODUCING ABSORBENT STRUCTURES HAVING ABSORBENT PADS AND ABSORBENT INSERTS

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 536 days.

(21) Appl. No.: 18/183,416

(22) Filed: Mar. 14, 2023

(65) Prior Publication Data

US 2023/0293356 A1     Sep. 21, 2023

(30) Foreign Application Priority Data

Mar. 16, 2022     (IT) ......................... 102022000005171

(51) Int. Cl.
*A61F 13/15*     (2006.01)

(52) U.S. Cl.
CPC ................................ *A61F 13/1565* (2013.01)

(58) Field of Classification Search
CPC ...... A61F 2013/4518; A61F 2013/4525; A61F 2013/4531; A61F 2013/4537; A61F 2013/4543; A61F 203/4568; A61F 2013/4581; A61F 2013/4587; A61F 13/47218; A61F 2013/4729; A61F 13/505; A61F 2013/5055; A61F 2013/53782
See application file for complete search history.

(56) References Cited

U.S. PATENT DOCUMENTS

| | | | | |
|---|---|---|---|---|
| 5,891,120 A | * | 4/1999 | Chmielewski | ........ A61F 13/535 604/378 |
| 6,037,518 A | * | 3/2000 | Guidotti | .............. A61F 13/5376 604/385.101 |
| 2003/0118764 A1 | * | 6/2003 | Adams | ................... A61F 13/535 428/36.9 |
| 2003/0135177 A1 | * | 7/2003 | Baker | ................... A61F 13/535 604/386 |
| 2023/0007888 A1 | * | 1/2023 | Sablone | .............. A61F 13/5116 |
| 2023/0293362 A1 | * | 9/2023 | Sablone | ............ A61F 13/15617 604/378 |
| 2024/0180754 A1 | * | 6/2024 | Sablone | ................... A61F 13/47 |

FOREIGN PATENT DOCUMENTS

| | | |
|---|---|---|
| EP | 2949300 A1 | 12/2015 |
| EP | 3153141 A1 | 4/2017 |
| EP | 3453368 A1 | 3/2019 |
| EP | 3552591 A1 | 10/2019 |
| WO | 2022034468 A1 | 2/2022 |

OTHER PUBLICATIONS

Search Report dated Oct. 31, 2022. 8 pages.

* cited by examiner

*Primary Examiner* — Michele Kidwell
(74) *Attorney, Agent, or Firm* — RMCK Law Group PLC

(57) ABSTRACT

A method for producing absorbent structures, including forming an array of absorbent pads having cellulose fluff, forming an array of fluff-free absorbent inserts, and inserting the fluff-free absorbent inserts into respective through-openings of absorbent pads.

3 Claims, 12 Drawing Sheets

METHOD FOR PRODUCING ABSORBENT STRUCTURES HAVING ABSORBENT PADS AND ABSORBENT INSERTS

CROSS-REFERENCE TO RELATED APPLICATION

This application claims priority to Italian Patent Application No. 102022000005171 filed Mar. 16, 2022. The disclosure of the above application is incorporated herein by reference in its entirety.

FIELD OF THE INVENTION

The present invention relates to a method for producing absorbent structures for sanitary articles.

The invention was developed in particular with a view to its application for producing absorbent sanitary articles such as, for example, diapers and diaper-pants for babies, incontinence pads for adults, sanitary towels for women, and similar sanitary articles intended to absorb body fluids.

The present invention may also be used for producing plasters and similar sanitary articles for covering wounds.

DESCRIPTION OF THE PRIOR ART

The absorbent sanitary articles typically have a layered structure comprising an outer sheet or backsheet impervious to liquids, an inner sheet or topsheet permeable to liquids and intended to be placed in contact with the user's skin, and an absorbent structure that has the function of capturing and storing body fluids.

The absorbent structure often comprises superabsorbent granular materials. These superabsorbent materials are known by various names such as, for example, SAP (Super Absorbent Polymer) or AGM (Absorbent Gelling Material). In most cases, hydro gelling materials are used that are capable of absorbing and capturing the liquid.

Most absorbent structures of absorbent sanitary articles currently on the market belong to one of the following two categories:

- absorbent core formed by cellulose fluff, obtained from defibrated cellulose, mixed with superabsorbent granular material;
- fluff-free absorbent core formed by one or more non-woven webs with superabsorbent granular material deposited on the surface or trapped inside the non-woven webs.

In recent years there has been a strong demand for more flexible, thinner, lighter and more absorbent sanitary articles, and this has led to the development of fluff-free absorbent cores which have gradually been employed to replace absorbent cores formed from cellulose fluff mixed with superabsorbent granular material.

EP-A-3153141 by the same applicant describes a method for producing a fluff-free absorbent structure for absorbent sanitary articles, wherein superabsorbent granular material is distributed on a non-woven layer with fibers bound by hot air (Air Through Bonding or ATB) and wherein the non-woven layer is volumized by a toothed portion that raises and opens the fibers to favor the penetration of the particles of superabsorbent material inside the bound fibers of the non-woven layer.

The evolution of the market towards fluff-free absorbent cores has prompted many manufacturers of absorbent sanitary articles and raw materials to develop sheets of ATB (Air Through Bonding) material, which are more suitable for producing absorbent cores in terms of capacity to trap particles of SAP and in terms of softness to give softness to the absorbent core in the absence of cellulose fluff. To fulfill these functions, ATB materials must be very bulky and, therefore, the sheets are very thick and this leads to several problems, including:

- the transport of these materials is not very efficient because the mass/volume ratio is very low;
- the duration of the reels in the machine is very low and involves problems related to frequent reel changes.

Furthermore, fluff-free absorbent cores generally have a high absorbency, and the absorbent core may expand several times its weight and volume. These increases may cause the absorbent article to deform and/or sag in the crotch region as they become saturated with liquid. This may cause leaks through the edges of the absorbent core.

EP3453368A1 discloses an absorbent core comprising cellulose fluff or fluff-free wrapped between a topsheet and a backsheet, wherein at least one attachment zone is provided between the absorbent core, the topsheet and the backsheet, in which no absorbent material is present.

OBJECT AND SUMMARY OF THE INVENTION

The present invention aims to provide a method for producing absorbent structures that overcomes the problems of the prior art.

According to the present invention, this object is achieved by a method having the characteristics forming the subject of claim 1.

The claims form an integral part of the technical disclosure provided in relation to the invention.

BRIEF DESCRIPTION OF THE DRAWINGS

The invention will now be described in detail with reference to the attached drawings, given purely by way of non-limiting example, wherein.

It will be appreciated that the various figures may not be represented on the same scale. It will also be appreciated that some elements or components may not be illustrated to make other elements/components more visible and to simplify the understanding of the figures.

DETAILED DESCRIPTION

Figure 1:
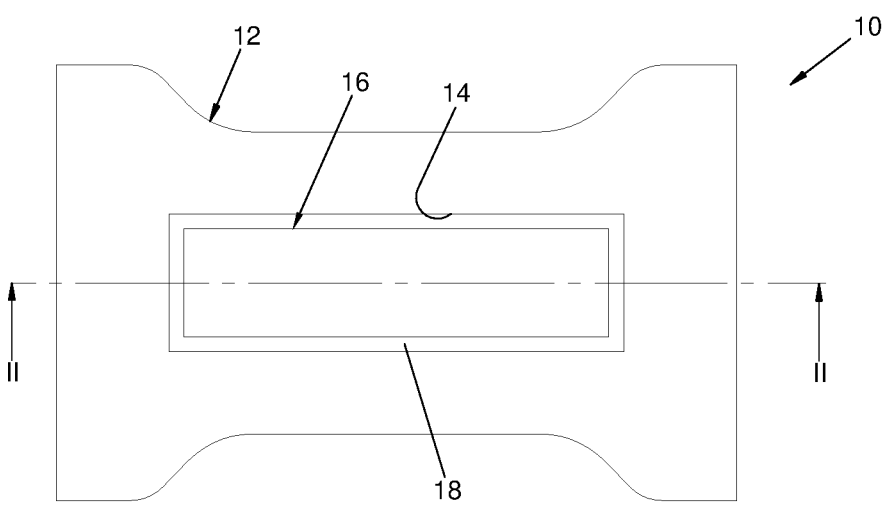
FIG. 1 is a plan schematic view of an embodiment of an absorbent structure according to the present invention.
Figure 2:
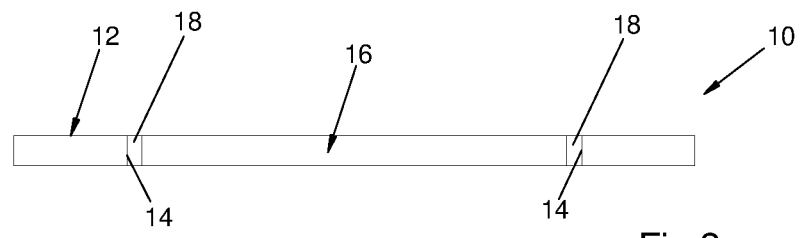
FIG. 2 is a schematic cross-section along the line II-II of FIG. 1.

With reference to FIGS. 1 and 2, numeral 10 indicates an absorbent structure according to the present invention.

The absorbent structure 10 comprises an absorbent pad 12 comprising cellulose fluff. The absorbent pad 12 may be formed exclusively of cellulose fluff or of a mixture of cellulose fluff and superabsorbent material, both in granular form and/or in fibers also known as Super Absorbent Fibers (SAF). The absorbent pad 12 has at least one through-opening 14.

The absorbent structure 10 comprises at least one fluff-free absorbent insert 16 inserted in the through-opening 14 of the absorbent pad 12, so that the fluff-free absorbent insert 16 is surrounded by cellulose fluff, optionally mixed with superabsorbent material. The superabsorbent material may be granular or fibrous (SAF).

The fluff-free absorbent insert 16 is formed by a non-woven layer wherein the superabsorbent material is incorporated. The fluff-free absorbent insert 16 may comprise fibers normally used for producing non-woven webs such as:
- synthetic fibers such as polyester, polyethylene, polypropylene, polyurethane, polyamide, acrylate, cellulose acetate, cupro, lyocell, modal, viscose or rayon, or their mixtures, or
- natural fibers such as cotton, linen, hemp, jute, ramie, coconut, pineapple, gorse, hibiscus, straw, bamboo, soy, kapok, eucalyptus, or their mixtures.

A gap 18 is formed between the absorbent pad 12 and the fluff-free absorbent insert 16, which may have a width of between 0.1 and 20 mm, and preferably between 4 and 10 mm.

Figure 14:
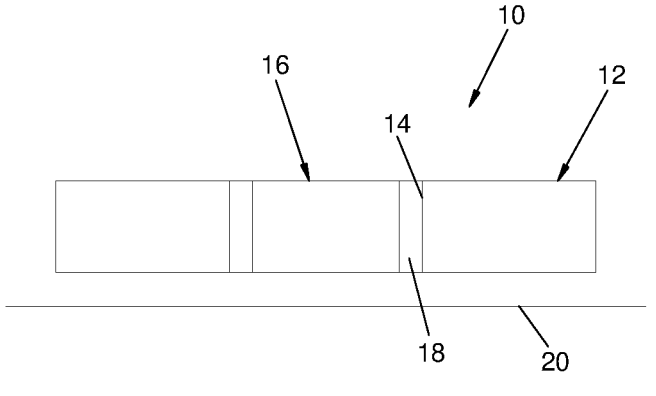
FIG. 14 is a schematic cross-section of a possible embodiment of an absorbent structure according to the present invention.

With reference to FIG. 14, the absorbent structure 10 may comprise a non-woven web 20 to which at least one fluff-free absorbent insert 16 may be fixed, for example, by glue.

Figure 3:
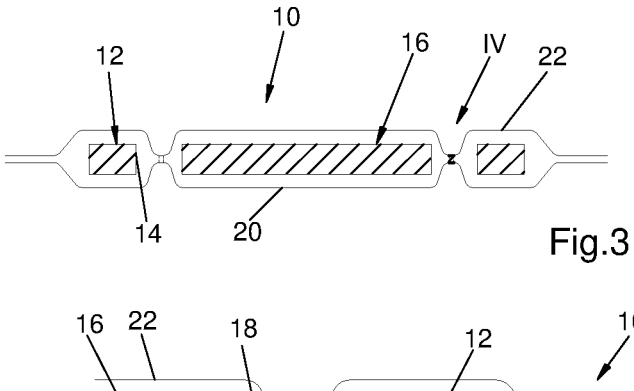
FIG. 3 is a schematic cross-section illustrating a possible embodiment of an absorbent structure according to the present invention.
Figure 4:
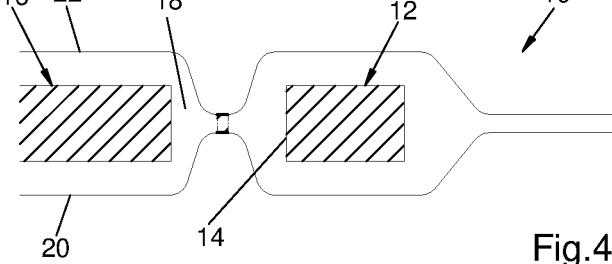
FIG. 4 is an enlarged detail of the part indicated by the arrow IV in FIG. 3.

With reference to FIGS. 3 and 4, the absorbent structure 10 may comprise two non-woven webs 20, 22, which enclose the absorbent pad 12 and at least one fluff-free absorbent insert 16 in a sandwich-like manner. The two non-woven webs 20, 22 may be fixed together along the outer perimeter of the absorbent pad 12 and through the gap 18 formed between the absorbent pad 12 and the fluff-free absorbent insert 16. The fastening between the two non-woven webs 22 may be carried out by welding (thermal or ultrasonic) or by glue. The welding between the two non-woven webs 20, 22 may be achieved at least along the longitudinal sections of the gap 18.

Figure 5:
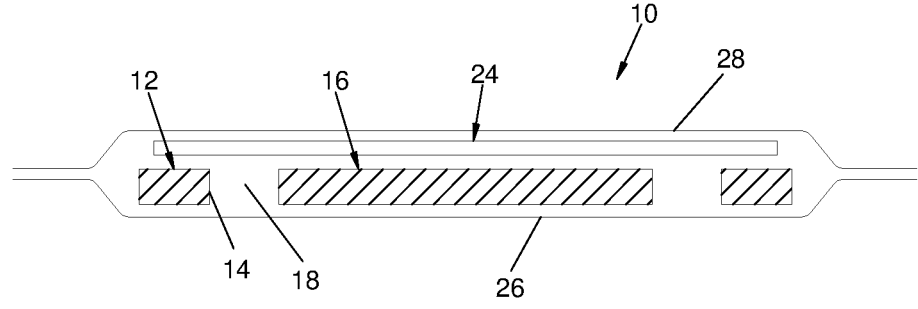
FIG. 5 is a schematic cross-section illustrating another embodiment of an absorbent structure according to the present invention.

With reference to FIG. 5, the absorbent structure 10 may comprise at least one acquisition and distribution layer 24 arranged on a surface of the assembly formed by the absorbent pad 12 and by at least one fluff-free absorbent insert 16. The acquisition and distribution layer 24 has the object of uniformly distributing the liquids on the surfaces of the absorbent pad 12 and of the fluff-free absorbent insert 16, and may consist of one or more high-volume non-woven layers, for example, Air Through Bonding, free from absorbent material. The absorbent structure 10 may be sandwiched between a backsheet 26 and a topsheet 28.

With reference to FIGS. 6-13, the absorbent structure 10 may have different geometries.

Figure 6:
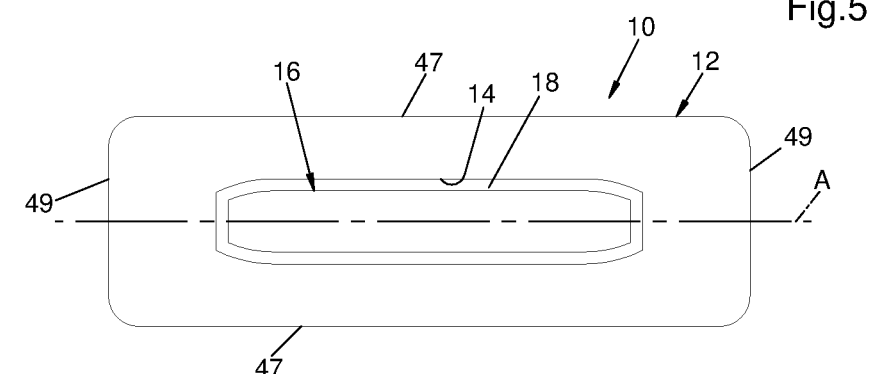
FIGS. 6-13 are schematic plan views of possible embodiments of absorbent structures according to the present

With reference to FIG. 6, the absorbent pad 12 may have an elongated shape along a longitudinal axis A. The absorbent pad 12 may have two longitudinal sides 47 parallel to the longitudinal axis A, and two transversal sides 49 perpendicular to the longitudinal axis A. The absorbent pad 12 may have only one through-opening 14 elongated along the longitudinal axis A. The through-opening 14 may be symmetrical with respect to the longitudinal axis A. The through-opening 14 may have two longitudinal sides parallel to the longitudinal axis A and two transverse sides perpendicular to the longitudinal axis A. The absorbent structure 10 may have a single fluff-free absorbent insert 16 inserted into the through-opening 14. The fluff-free absorbent insert 16 may have a shape corresponding to that of the through-opening 14.

Figure 9:
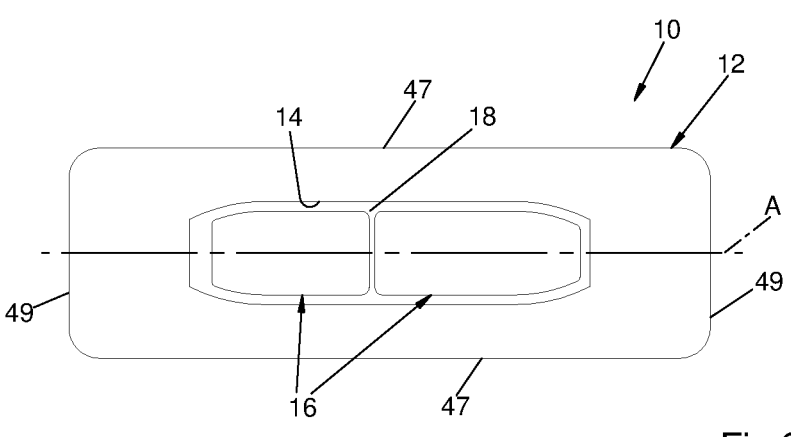

In the embodiment of FIG. 9, the absorbent pad 12 may have the same shape as that of FIG. 6, with a single through-opening 14 elongated along the longitudinal axis A of the absorbent pad 12. In the embodiment of FIG. 9 the absorbent structure 10 may have two fluff-free absorbent inserts 16 inserted in the same through-opening 14. The two fluff-free absorbent inserts 16 may be aligned with each other along the longitudinal axis A.

Figure 7:
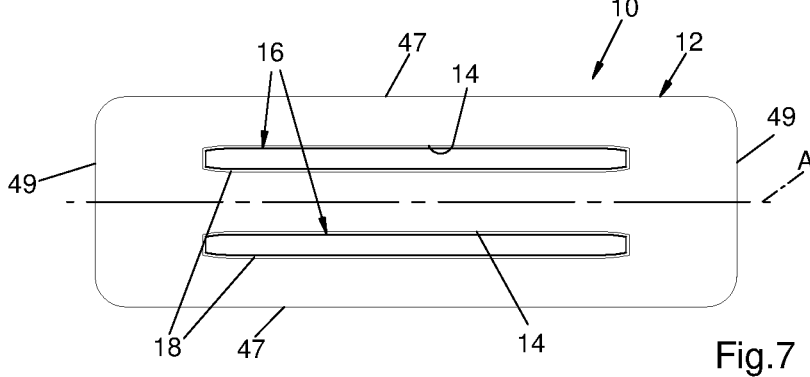

In the embodiment of FIG. 7, the absorbent pad 12 may have two through-openings 14 parallel to each other and elongated along respective directions parallel to the longitudinal axis A. The two through-openings 14 may be arranged on opposite sides of the longitudinal axis A. In the embodiment of FIG. 7, the absorbent structure 10 may have two fluff-free absorbent inserts 16 inserted into the respective through-openings 14. The two through-openings 14 and the respective fluff-free absorbent inserts 16 may have a straight shape, with the respective longitudinal sides parallel to the longitudinal axis A.

Figure 10:
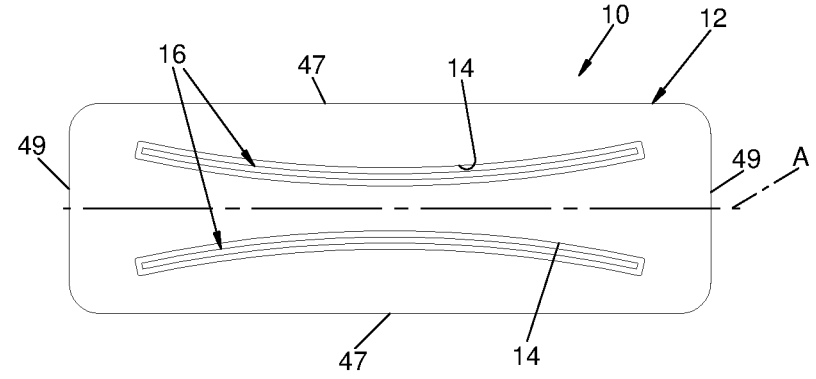

In the embodiment illustrated in FIG. 10 the absorbent pad 12 may have two through-openings 14 each having at least one curved side. The two through-openings 14 may have two curved longitudinal sides with the concavities facing the respective longitudinal edge 47 of the absorbent pad 12. The two through-openings 14 may be arranged on opposite sides of the longitudinal axis A and may be specular with respect to the longitudinal axis A. In the embodiment of FIG. 10, the absorbent structure 10 may have two fluff-free absorbent inserts 16 inserted within the respective through-openings 14, and have shapes corresponding to those of the through-openings 14.

Figure 8:
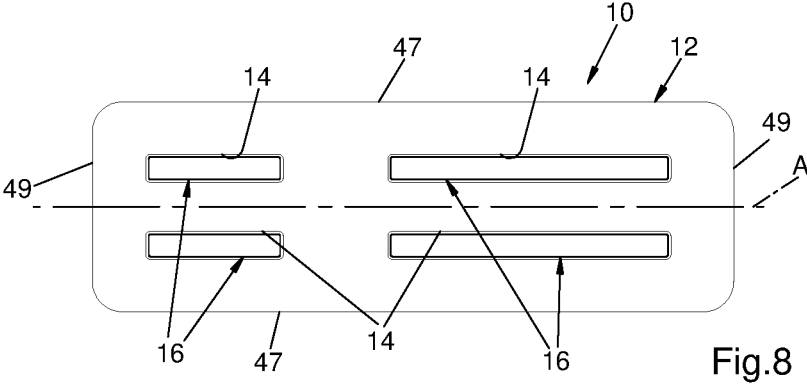

In the embodiment of FIG. 8, the absorbent pad 12 may have two pairs of through-openings 14. Each pair comprises two through openings 14 parallel to each other, located on opposite sides of the longitudinal axis A and symmetrical with respect to the longitudinal axis A. Each of the through-openings 14 may be aligned with an opening of the other pair and spaced apart from it along the longitudinal axis A. The through-openings 14 may have respective longitudinal sides parallel to the longitudinal axis A of the absorbent pad 12, and may be extended along respective directions parallel to the longitudinal axis A. In the embodiment of FIG. 8, the absorbent structure 10 may have four fluff-free absorbent inserts 16 inserted into the respective through-openings 14 and having shapes corresponding to those of the through-openings 14.

Figure 11:
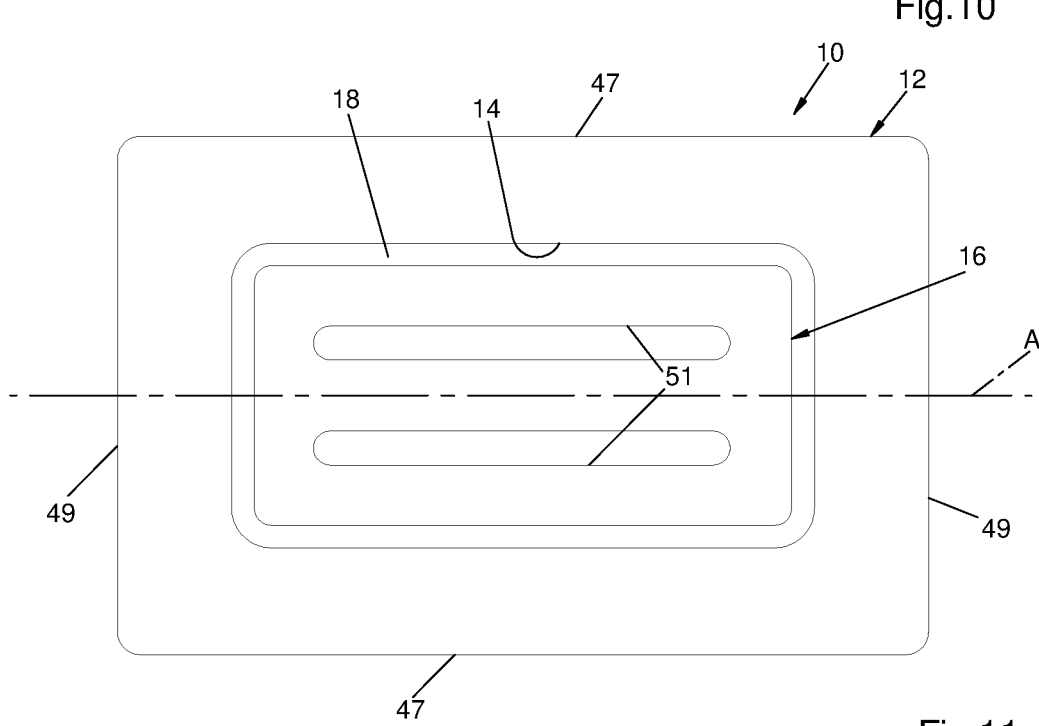

In the embodiment of FIG. 11 the absorbent pad 12 may have only one through-opening symmetrical with respect to the longitudinal axis A. The through-opening 14 may have two longitudinal sides and two transverse sides, parallel— respectively—to the longitudinal sides 47 and to the transverse sides 49 of the absorbent pad 12. The absorbent structure 10 may have only one fluff-free absorbent insert 16. The fluff-free absorbent insert 16 may be provided with recesses or openings 51. For example, the fluff-free absorbent insert 16 may have two recesses or openings 51 elongated along the longitudinal axis A and arranged symmetrically with respect to the longitudinal axis A.

Figure 12:
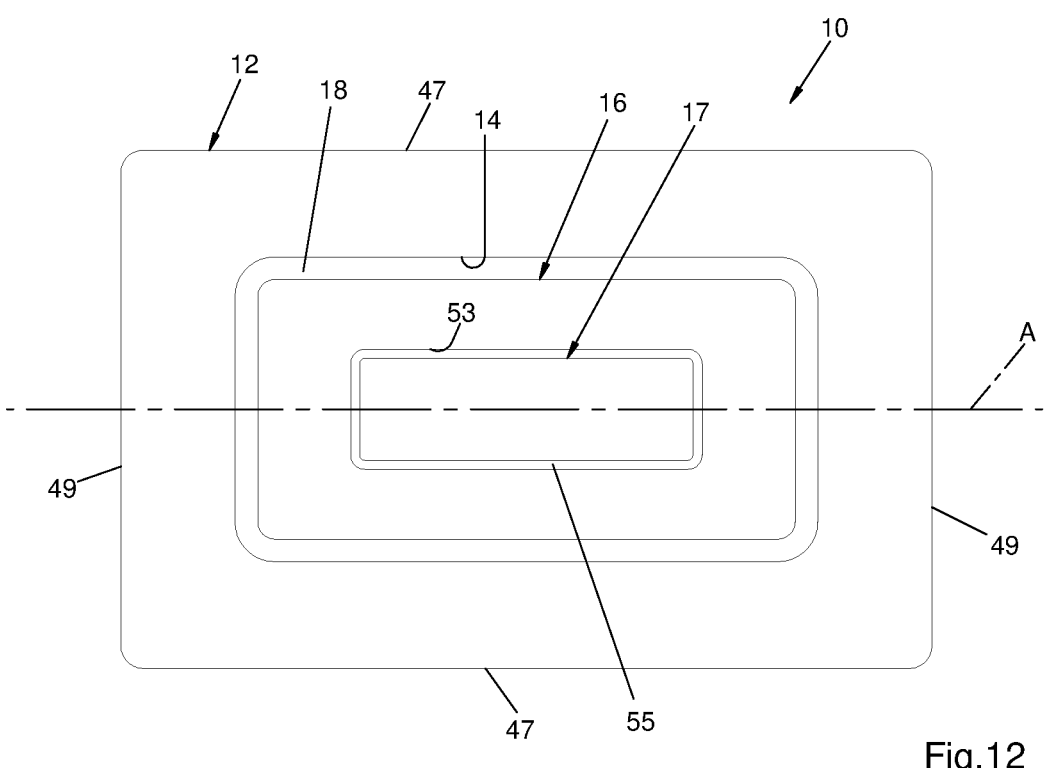

With reference to FIG. 12, the absorbent structure 10 may comprise a first fluff-free absorbent insert 16 inserted into a through-opening 14 of the absorbent pad 12 and having a through-opening 53. The absorbent structure 10 may comprise a second fluff-free absorbent insert 17 inserted into the through-opening 53 of the first fluff-free absorbent insert 16. A second gap 55 may be formed between the first fluff-free absorbent insert 16 and the second fluff-free absorbent insert 17.

Figure 13:
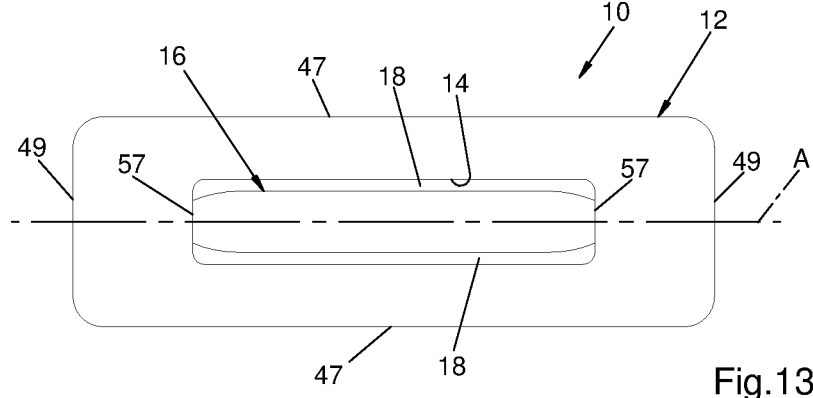

In the embodiment of FIG. 13, the fluff-free absorbent insert 16 may have transverse sides 57 that touch or overlap with corresponding transverse sides of the through-opening 14. In this case, the gap 18 extends only along the longitudinal sides of the through-opening 14 of the absorbent pad 12.

Figure 17:
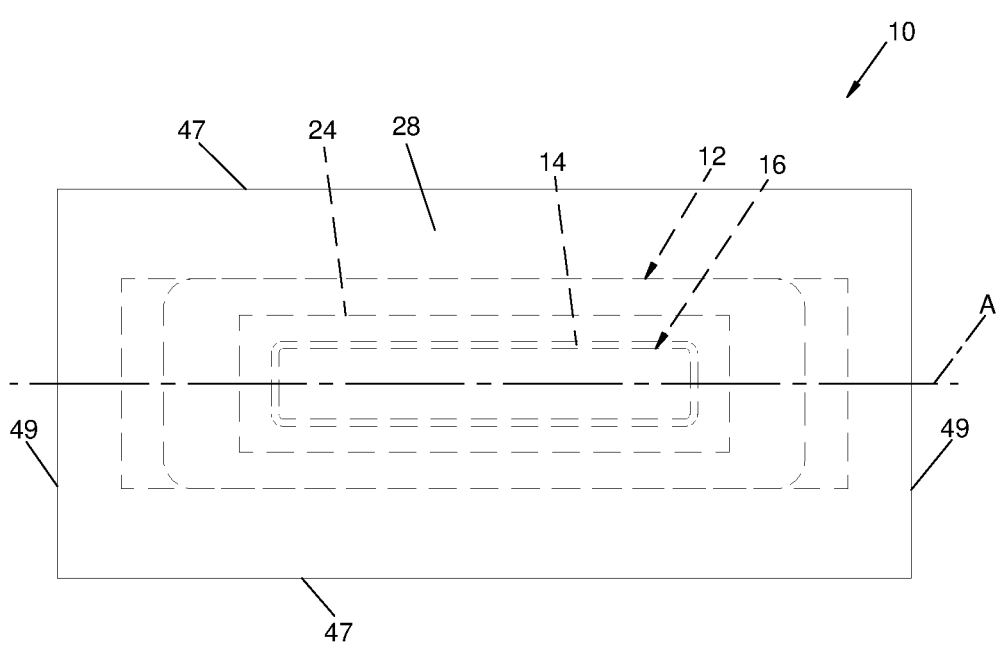
FIG. 17 is a schematic plan view of another possible embodiment of an absorbent structure according to the present invention.
Figure 18:
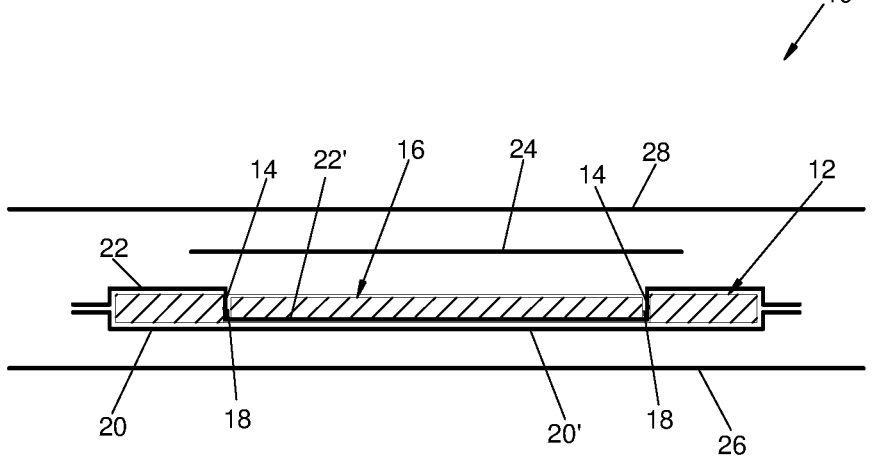
FIG. 18 is a schematic cross-section along the line XVIII-XVIII of FIG. 17, and FIGS. 19-24 are schematic views illustrating possible embodiments of methods for producing absorbent structures according to the present invention.

With reference to FIGS. 17 and 18, in a possible embodiment, the absorbent structure 10 may comprise two non-woven webs 20, 22 sandwiching the absorbent pad 12. The two non-woven webs 20, 22 have respective portions 20', 22' superimposed on each other inside the through-opening 14. The two non-woven webs 20, 22 may be fixed together along the outer perimeter of the absorbent pad 12 and through the through-opening 14. The fastening between the two non-woven webs 22 may be carried out by welding (thermal or ultrasonic) or by glue.

With reference to FIG. 18, in this embodiment the fluff-free absorbent insert 16 is housed in the through-opening 14 of the absorbent pad 12 superimposed on the two portions 20', 22' of the two non-woven webs 20, 22 that extend inside the through-opening 14.

In the embodiment of FIGS. 17 and 18, the absorbent structure 10 may comprise at least one acquisition and distribution layer 24 arranged outside the two non-woven webs 20, 22 on a surface of the assembly formed by the absorbent pad 12 and at least one fluff-free absorbent insert 16. The absorbent structure 10 may be sandwiched between a backsheet 26 and a topsheet 28.

The different geometries of the various embodiments previously described may be combined with each other in various ways. Furthermore, in one or more of the embodiments previously described the following variants may be provided:

the fluff-free absorbent insert 16 may be centered with respect to the through-opening 14 of the absorbent pad 12;

the fluff-free absorbent insert 16 may be decentralized with respect to the through-opening 14 of the absorbent pad 12 so as to generate a gap 18 with a variable thickness;

if several fluff-free absorbent inserts 16, 17 are provided, these can be misaligned with each other and generate one or more gaps 18 with variable thickness;

in the case wherein several fluff-free absorbent inserts 16, 17 are provided, the concentrations of superabsorbent material, whether in granular form and/or in fibers also called Superabsorbent Fibers (SAF), may be different from each other;

the thicknesses of the various components (absorbent pad 12 and fluff-free absorbent inserts 16, 17) may be different from each other;

if several fluff-free absorbent inserts 16, 17 are provided, these may be partially superimposed on each other;

if the absorbent pad 12 has a plurality of through-openings 14, a fluff-free absorbent insert 16 is inserted in at least one of the through-openings 14, and at least one of the through-openings 14 is without a fluff-free absorbent insert 16.

Figure 15:
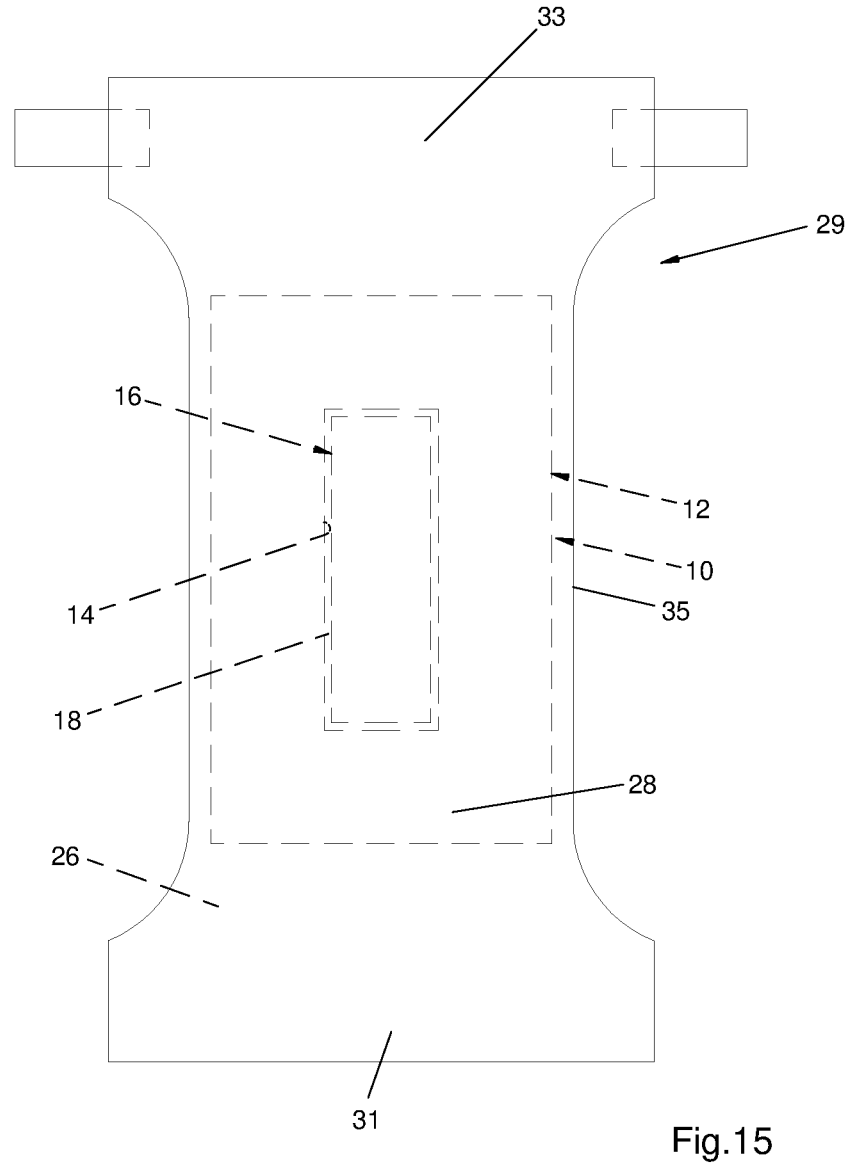
FIG. 15 is a schematic plan view of an absorbent sanitary article including an absorbent structure according to the present invention, invention.

With reference to FIG. 15, the absorbent structure 10 may be included in an absorbent sanitary article 29. The absorbent sanitary article 29 may have front and rear waist sections 31, 33 closable around the wearer's waist, and a crotch section 35, which extends between the front and rear waist sections 31, 33. The absorbent sanitary article 29 may comprise a topsheet 28 which—in use—faces the user and a backsheet 26 which—in use—faces away from the user. The absorbent structure 10 may be sandwiched between the topsheet 28 and the backsheet 26, and may extend into the crotch section 35 between the front and rear waist sections 31, 33.

Figure 16:
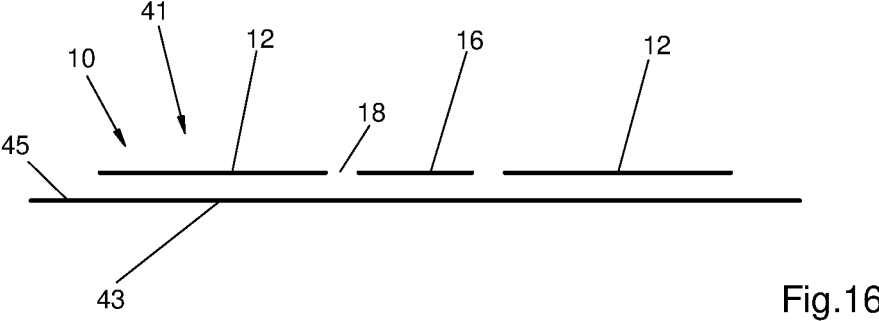
FIG. 16 is a schematic cross-section of a plaster including an absorbent structure according to the present invention.

With reference to FIG. 16, the absorbent structure 10 may be included in a plaster 41. The plaster 41 may have a support sheet 43 with an adhesive surface 45 on which the absorbent structure 10 can be applied.

Figure 19:
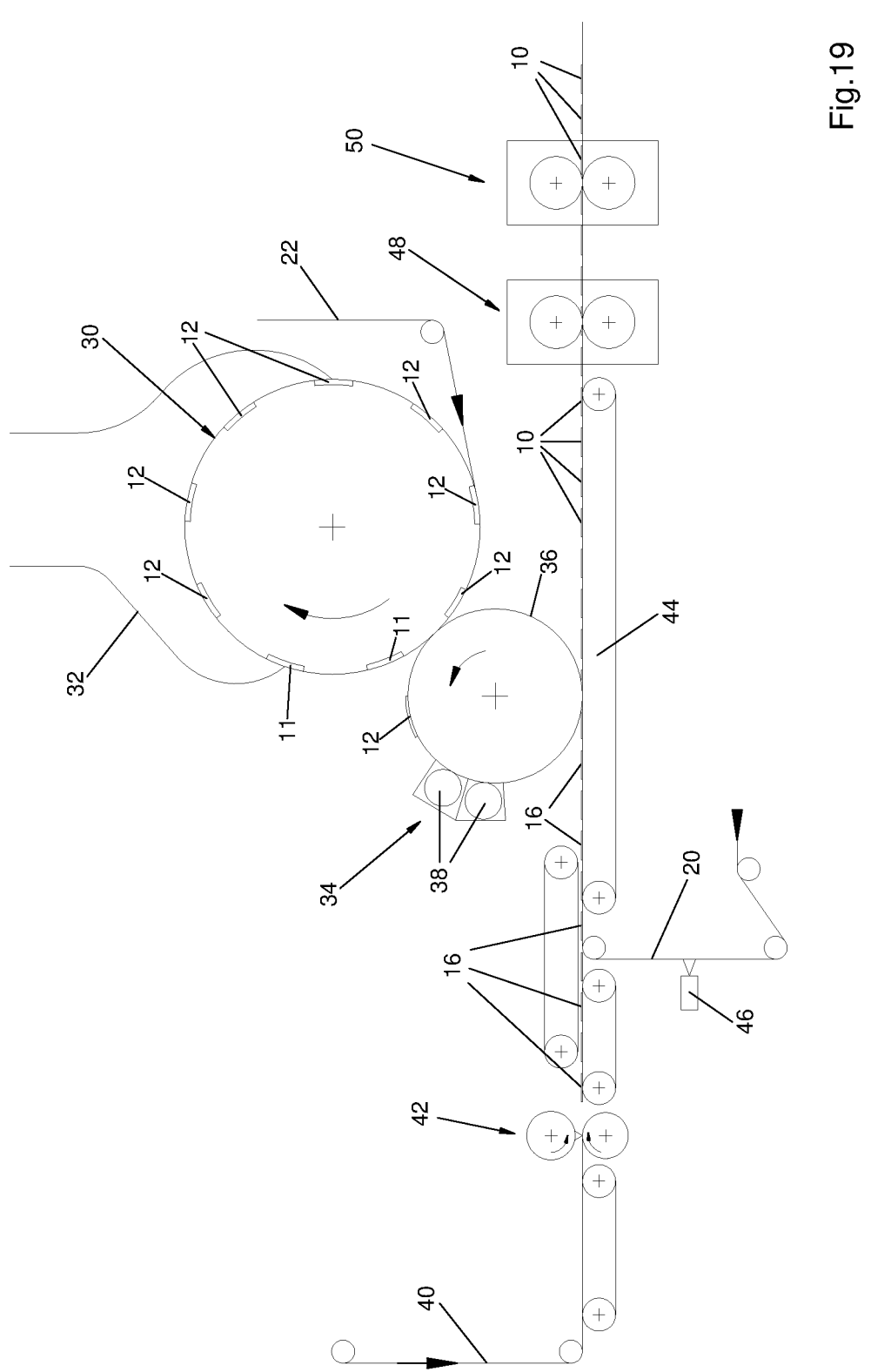

FIG. 19 schematically illustrates a method for producing absorbent structures 10 as previously described.

The method for producing absorbent structures 10 comprises the formation of an array of fluff-free absorbent inserts 16 comprising a non-woven layer in which superabsorbent material is incorporated.

The array of fluff-free absorbent inserts 16 is obtained starting from a continuous fluff-free absorbent web 40 formed by one or more non-woven layers wherein fibrous or granular superabsorbent material is incorporated.

The fibers used for producing the fluff-free absorbent continuous web 40 may be joined together mechanically (for example, by needle punching), with adhesives or with thermal processes, using conventional techniques in the sector, such as Air Through Bonding, Spunbond, Meltblown, etc.

The superabsorbent material may be granular and may be dispersed among the fibers of the continuous fluff-free absorbent web 40, for example, with the techniques described in WO2022/034468 and EP-A-3153141 by the same Applicant. The superabsorbent material may also be in the form of fibers (superabsorbent fibers or SAF) mixed with the fluff-free fibers.

In a possible embodiment, the continuous fluff-free absorbent web 40 may be formed off-line and collected in reels that feed the apparatus for producing absorbent structures. In a possible embodiment, the fluff-free absorbent continuous web 40 may be formed by an apparatus (for example, as described in WO2022/034468 or EP-A-3153141) arranged in-line with the apparatus for producing absorbent structures.

The continuous fluff-free absorbent web 40 is cut transversely in a cutting unit 42 so as to form an array of fluff-free absorbent inserts 16 that advance spaced apart on a conveyor 44.

The fluff-free absorbent inserts 16 may be fixed on a first continuous non-woven web 20 in mutually spaced apart positions along a longitudinal direction. A glue applicator 46 may be provided to apply glue on the first continuous non-woven web 20 in phase with the fluff-free absorbent inserts 16.

The method for producing absorbent structures 10 comprises forming an array of absorbent pads 12 having respective through-openings. The absorbent pads 12 may be formed from cellulose fluff or from a mixture of cellulose fluff and superabsorbent material, both in granular form and/or in fibrous form also known as Super Absorbent Fibers (SAF).

The array of absorbent pads 12 may be produced, for example, as described in EP-A-2775975 by the same Applicant. The apparatus for forming the absorbent pads 12 may comprise a forming wheel 30 rotatable around a rotation axis and provided with seats 11 with a shape corresponding to the shape of the absorbent pads 12. The forming wheel 30 may face a chamber 32 containing cellulose fluff and possibly granular superabsorbent polymers. The mixture of cellulose fluff and granular superabsorbent polymers is applied to the seats 11 of the forming wheel 30, and may be retained in the seats 11 by suction. The forming wheel 30 may face a chamber containing only cellulose fluff. The superabsorbent granular material, if provided, may be applied to the cellulose fluff deposited in the seats 11 of the forming wheel 30 by a powder dosing device. A second continuous non-woven web 22 may be applied to the forming wheel 30 above the absorbent pads 12.

At the exit of the forming wheel 30, the array of absorbent pads 12 may pass into a compression unit 34 including a transfer wheel 36, and one or more pressure rollers 38 that compress the absorbent pads 12 on the outer surface of the transfer wheel 36. A second continuous non-woven web 22 may be applied to the forming wheel 30 above the absorbent pads 12.

The method for producing absorbent structures 10 envisages arranging the absorbent pads 12 and the fluff-free absorbent inserts 16 in phase with each other and inserting the fluff-free absorbent inserts 16 into respective through-openings of the absorbent pads 12, so as to form an array of absorbent structures 10, each of which comprises an absorbent pad 12 and at least one fluff-free absorbent insert 16 inserted into a respective through-opening of the respective absorbent pad 12.

The transfer wheel 36 applies the absorbent pads 12 onto the conveyor 44 in phase with the fluff-free absorbent inserts 16, so that during the transfer of the absorbent pads 12 from the transfer wheel 36 to the conveyor 44 the fluff-free absorbent inserts 16 fit into the respective through-openings of the respective absorbent pads 12.

The absorbent pads 12 may be applied onto the second continuous non-woven web 22 in mutually spaced apart positions along a longitudinal direction. The transfer wheel 36 may superimpose the second non-woven web 22 onto the first non-woven web 20 on which the fluff-free absorbent inserts 16 are fixed. During the overlapping of the first and second continuous non-woven webs 20, 22, the fluff-free absorbent inserts 16 are inserted into respective through-openings 14 of the absorbent pads 12 and the array of absorbent pads 12 and fluff-free absorbent inserts 16 is sandwiched between the first and second continuous non-woven webs 20, 22.

There is a clearance between the fluff-free absorbent inserts 16 and the respective through-openings of the absorbent pads 12, whereby a gap 18 (FIG. 1) is formed that surrounds the fluff-free absorbent inserts 16.

The array of absorbent structures 10 thus formed may be sent to a welding unit 48 that welds together the first and second continuous non-woven webs 20, 22 along the perimeter of the absorbent pads 12 and along the gap 18, thereby forming absorbent structures 10 as illustrated in FIGS. 3 and 4. The array of absorbent structures 10 may then pass into a pressing unit 50.

Figure 20:
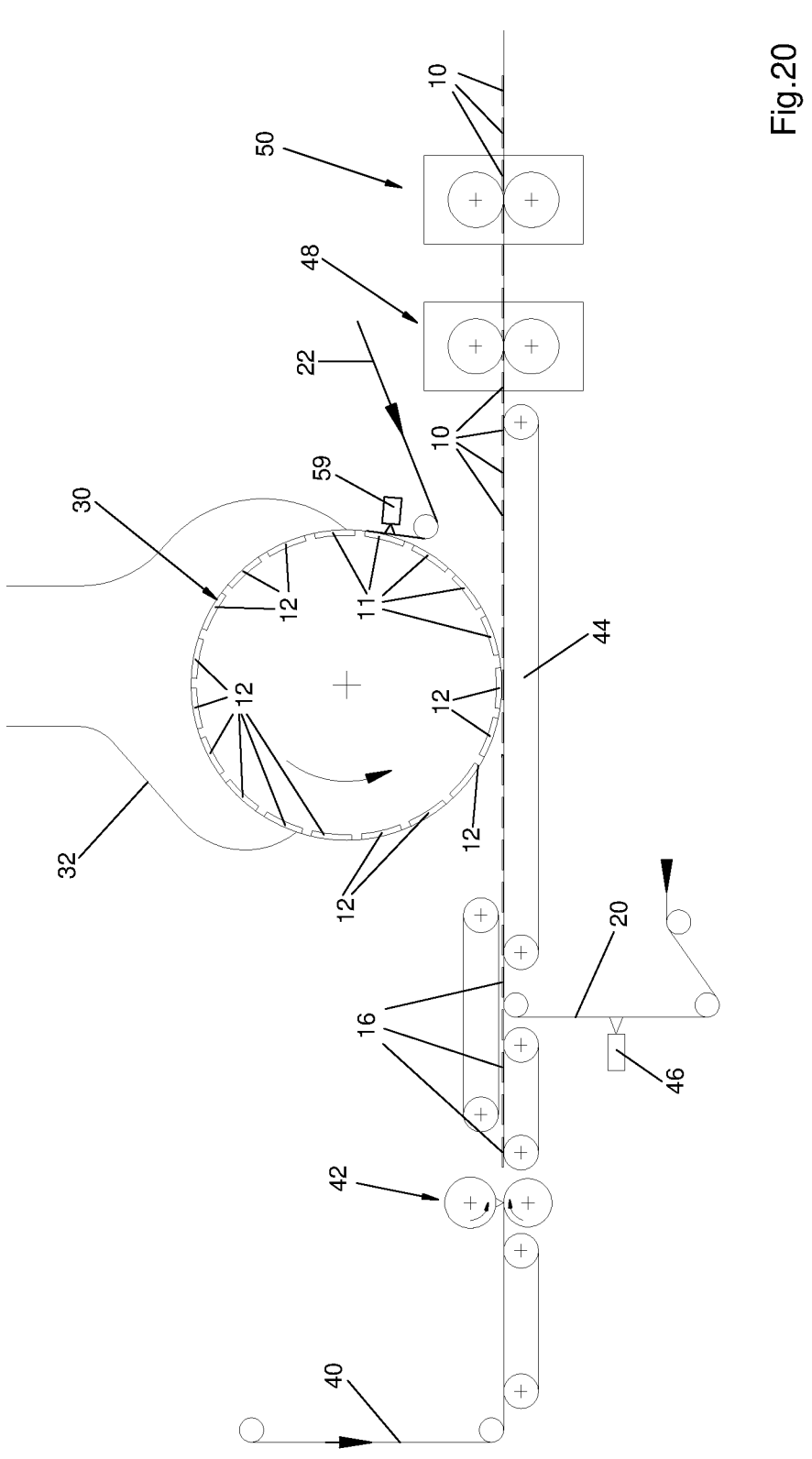

FIG. 20 illustrates a second embodiment of a method for producing absorbent structures. The elements corresponding to those previously described are indicated with the same numerical references.

In the embodiment of FIG. 20, the second continuous non-woven web 22 may be fed onto the surface of the forming wheel 30 upstream of the chamber 32 containing cellulose fluff and possibly granular superabsorbent polymers. In this embodiment, the mixture of cellulose fluff and possibly of granular superabsorbent polymers is applied onto the second continuous non-woven web 22 at the seats 11 of the forming wheel 30, and may be retained on the second continuous non-woven web 22 by suction. The absorbent pads 12 are, therefore, formed on the second continuous non-woven web 22 in mutually spaced apart positions along the longitudinal axis of the second continuous non-woven web 22. A glue applicator 59 may be provided to apply glue to the second continuous non-woven web 22 upstream of the chamber 32, so that the absorbent pads 12 are glued to the second continuous non-woven web 22.

In the embodiment of FIG. 20, a transfer wheel is not provided and the forming wheel 30 applies the absorbent pads 12 directly onto the conveyor 44 in phase with the fluff-free absorbent inserts 16. During the transfer of the absorbent pads 12 from the forming wheel 30 to the conveyor 44, the fluff-free absorbent inserts 16 are inserted into the respective through-openings of the respective absorbent pads 12.

Figure 21:
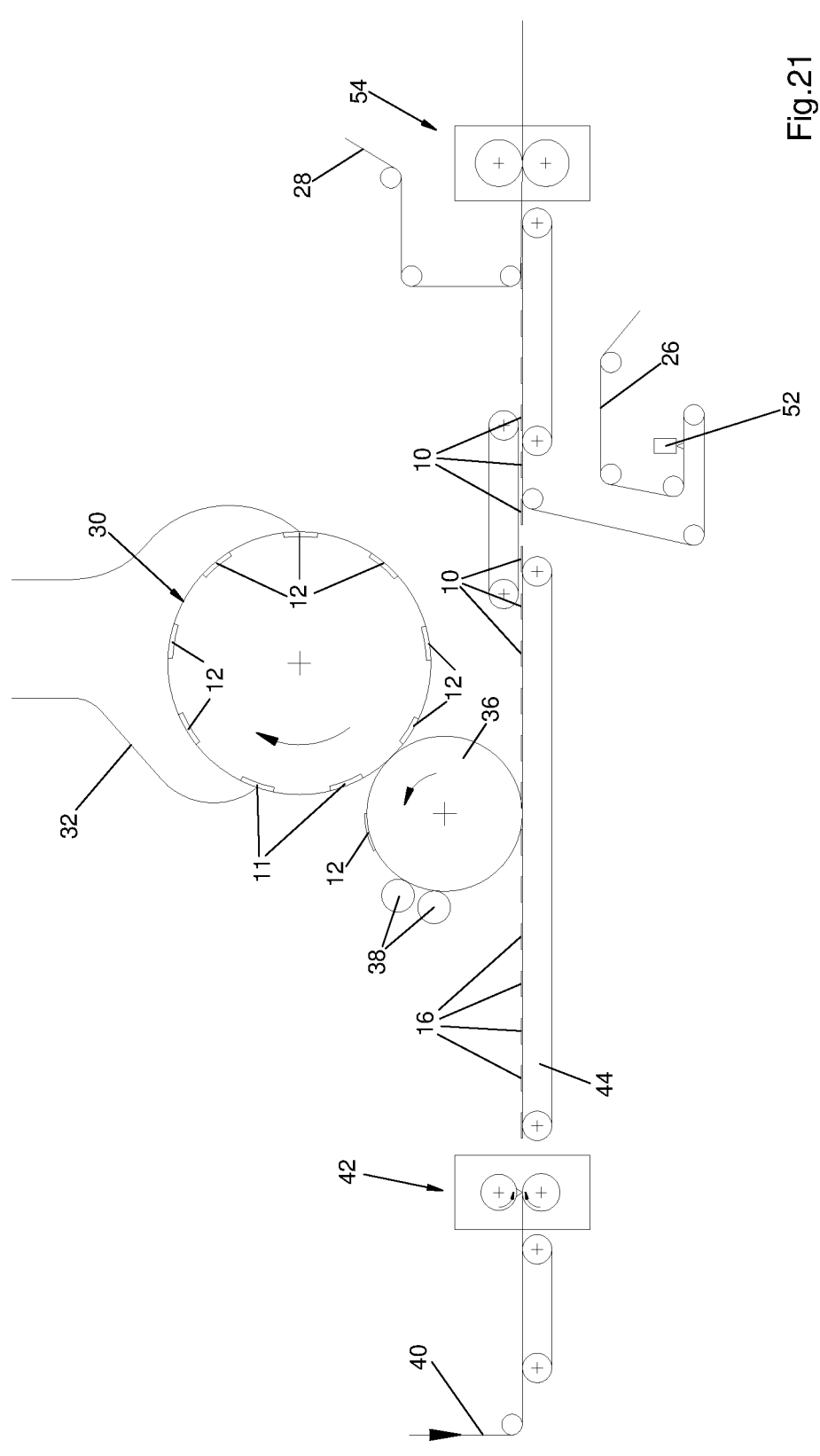

FIG. 21 illustrates a third embodiment of a method for producing absorbent structures.

In the embodiment of FIG. 21, the absorbent pads 12 and the fluff-free absorbent inserts 16 are not enclosed between two non-woven webs. The array of absorbent pads 12 formed as previously described is compressed onto the transfer wheel 36 without applying a non-woven web. The transfer wheel 36 applies the absorbent pads 12 onto the conveyor 44 in phase with the fluff-free absorbent inserts 16, so that during the transfer of the absorbent pads 12 from the transfer wheel 36 to the conveyor 44, the fluff-free absorbent inserts 16 fit into the respective through-openings of the respective absorbent pads 12. The array of absorbent structures 10 formed by the absorbent pads 12 and by the fluff-free absorbent inserts 16 is fixed onto a continuous backsheet web 26. A glue applicator 52 may be provided to apply glue onto the continuous backsheet web 26 in phase with the absorbent structures 10. Then, a continuous topsheet web 28 is applied over the continuous backsheet web 26 so as to sandwich the array of absorbent structures 10 between the continuous topsheet and backsheet webs 28, 26. A welding unit 54 may be provided to weld together the continuous topsheet and backsheet webs 28, 26 around absorbent structures 10.

Figure 22:
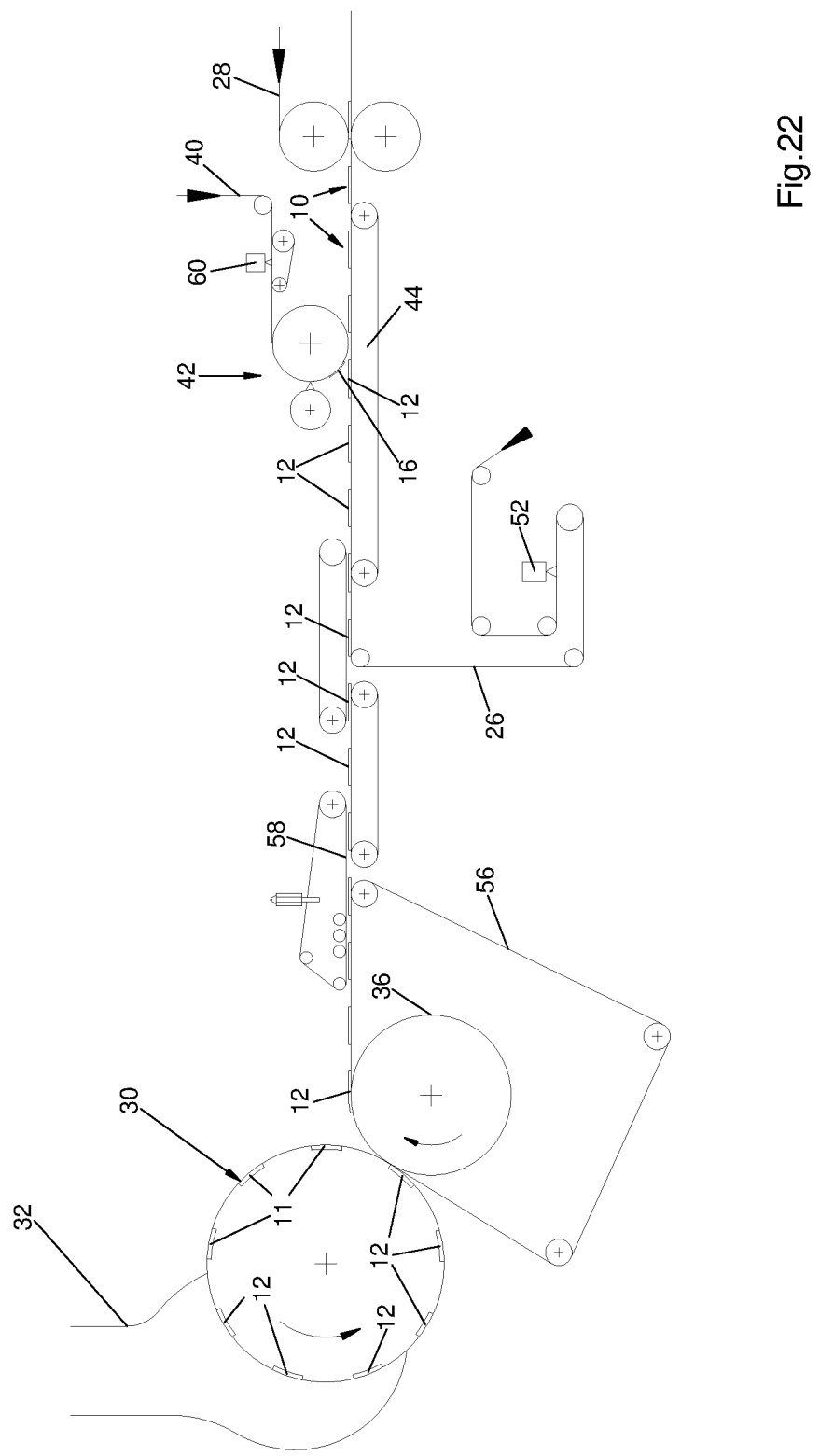

FIG. 22 illustrates a fourth embodiment of a method for producing absorbent structures.

In the embodiment of FIG. 22, the absorbent pads 12 at the exit from the forming wheel 30 are picked by a transfer belt 56, which moves around the transfer wheel 36 and are compressed between a compression belt 58 and the transfer belt 56. The array of absorbent pads 12 after compression is fixed onto a continuous backsheet web 26. A glue applicator 52 may apply glue onto the continuous backsheet web 26 in phase with the absorbent pads 12 so that the absorbent pads 12 are glued onto the backsheet web 26. The fluff-free absorbent inserts 16 are inserted into respective through-openings of the absorbent pads 12, while the array of absorbent pads 12 is fixed onto the continuous backsheet web 26. A glue applicator 60 may apply glue to the continuous fluff-free absorbent web 40 in phase with the absorbent pads 12 so that the fluff-free absorbent inserts 16, once inserted into the respective openings of the absorbent pads 12, are fixed by glue to the continuous backsheet web 26. Then, a continuous topsheet web 28 is applied over the continuous backsheet web 26 so as to sandwich the array of absorbent structures 10 between the continuous backsheet and topsheet webs 26, 28

Figure 23:
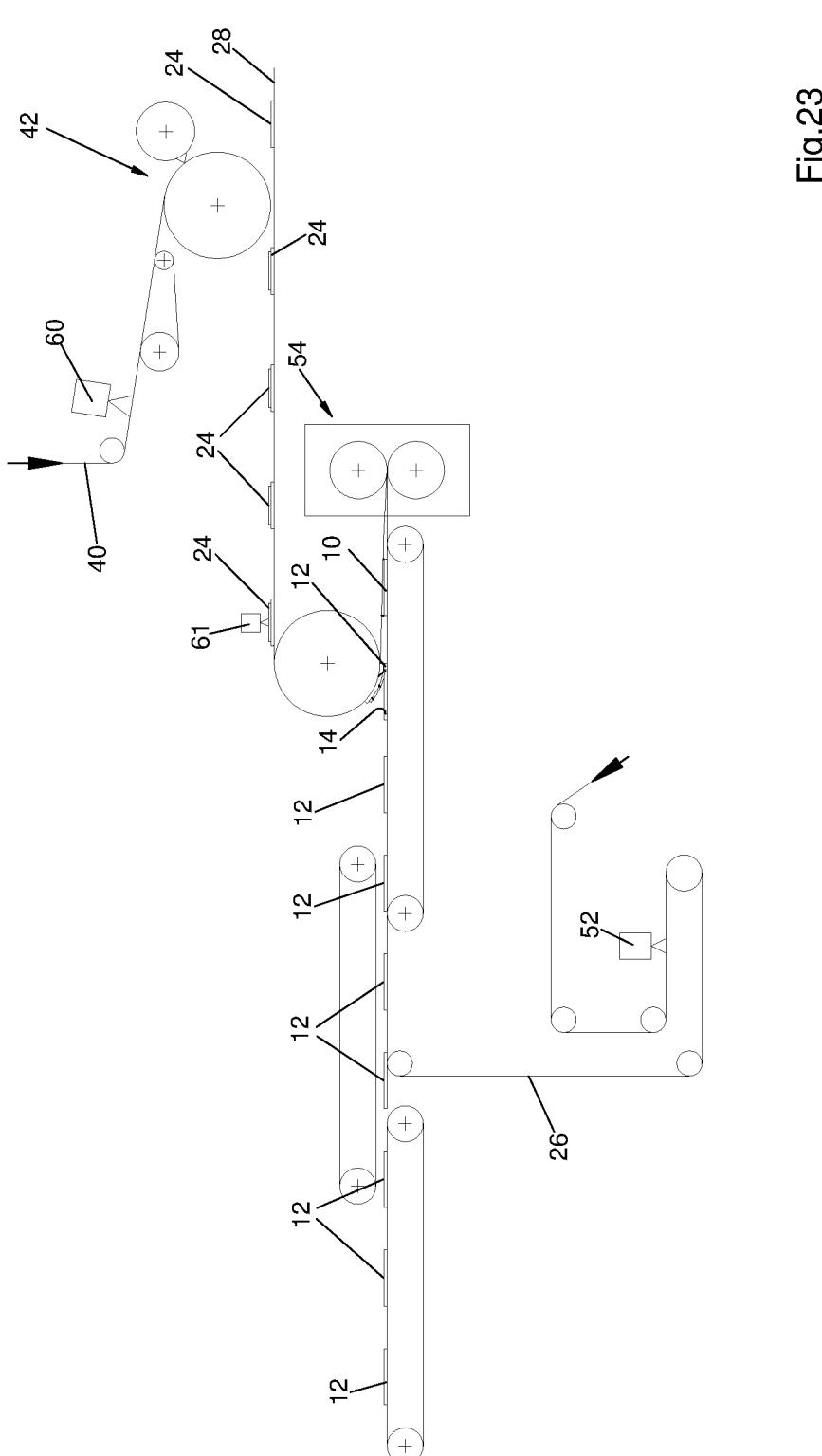

FIG. 23 illustrates a fifth embodiment of a method for producing absorbent structures.

In the embodiment of FIG. 23 the method comprises the formation of an array of acquisition and distribution layers 24 fixed on a continuous topsheet web 28 in positions spaced apart from each other in a longitudinal direction. The fluff-free absorbent inserts 16 are fixed onto the respective acquisition and distribution layers 24. A glue applicator 60 may apply glue onto the continuous fluff-free absorbent web 40 in phase with the acquisition and distribution layers 24 so that the fluff-free absorbent inserts 16, once applied onto the respective acquisition and distribution layers 24, are fixed to them by glue.

The array of absorbent pads 12 after a phase of compression is fixed onto a continuous backsheet web 26. A glue applicator 52 may apply glue to the continuous backsheet web 26 in phase with the absorbent pads 12 so that the absorbent pads 12 are glued onto the backsheet web 26.

The fluff-free absorbent inserts 16 fixed to respective acquisition and distribution layers 24 (in turn fixed to the continuous topsheet 28) inserted are into respective through-openings of the absorbent pads 12 while the absorbent pads 12 are fixed to the continuous backsheet web 26. A glue applicator 61 may apply glue onto the fluff-free absorbent inserts 16 before these are inserted into respective through-openings of the absorbent pads 12. A welding unit 54 may be provided to weld together the continuous topsheet and backsheet webs 28, 26 around the absorbent structures 10.

Figure 24:
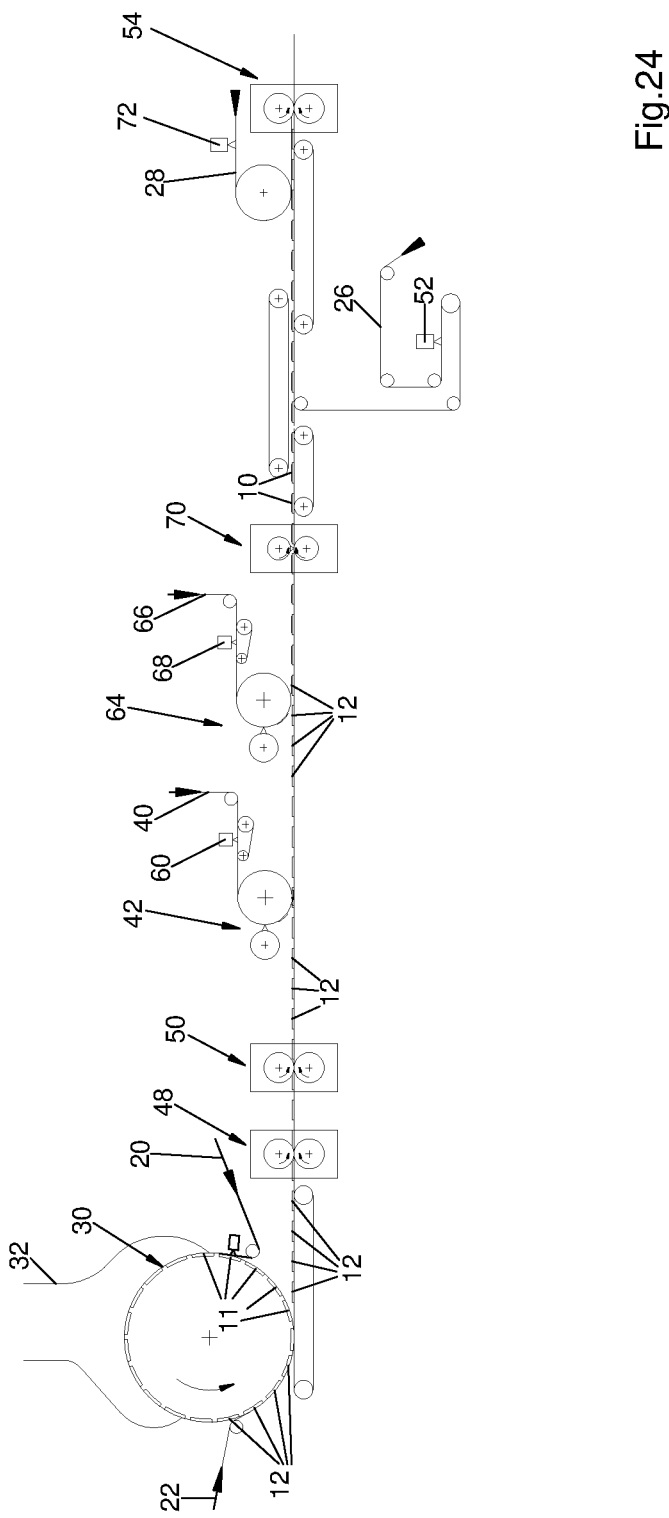

FIG. 24 illustrates a sixth embodiment of a method for producing absorbent structures.

In the embodiment of FIG. 24, the method envisages applying on the surface of the forming wheel 30 a first continuous non-woven web 20 upstream of the chamber 32 and a second continuous non-woven web 22 downstream of the chamber 32. In this embodiment, the absorbent pads 12 are formed on the first continuous non-woven web 20 and are sandwiched between the first and second continuous non-woven webs 20, 22.

The array of absorbent pads 12 enclosed between the first and second continuous non-woven webs 20, 22 may be sent to a welding unit 48, which welds together the first and second continuous non-woven webs 20, 22 around the perimeter and through the through-openings of the absorbent pads 12. The array of absorbent pads 10 may then pass into a pressing unit 50.

A continuous fluff-free absorbent web 40 is cut transversely in a cutting unit 42 so as to form an array of fluff-free absorbent inserts 16, which are inserted into respective openings of the absorbent pads 12 superimposed on the two continuous non-woven webs 20, 22. A glue applicator 60 may apply glue onto the continuous fluff-free absorbent web 40 in phase with the absorbent pads 12 so that the fluff-free absorbent inserts 16, once inserted into the respective openings of the absorbent pads 12, are fixed by glue to the two continuous non-woven webs 20, 22 superimposed on each other.

A second cutting unit 64 may be provided to transversely cut a continuous non-woven web 66 to form an array of acquisition and distribution layers 24, which are applied on respective fluff-free absorbent inserts 16. A glue applicator 68 may apply glue to the continuous non-woven web 66 in phase with the fluff-free absorbent inserts 16 so that the acquisition and distribution layers 24 may be glued to the respective assemblies formed by the absorbent pads 12 and the fluff-free absorbent inserts 16.

A cutting unit 70 may be provided to transversely cut the first and second continuous non-woven webs 20, 22 to form an array of discrete absorbent structures 10.

The array of absorbent structures 10 thus formed may be fixed onto a continuous backsheet web 26. A glue applicator 52 may be provided to apply glue to the continuous backsheet web 26 in phase with the absorbent structures 10. Then, a continuous topsheet web 28 may be applied over the continuous backsheet web 26 so as to sandwich the array of absorbent structures 10 between the continuous topsheet and backsheet webs 28, 26. A glue applicator 72 may be provided to apply glue to the continuous topsheet web 28. A welding unit 54 may be provided to weld together the continuous topsheet and backsheet webs 28, 26 around the absorbent structures 10.

The main advantages of the absorbent structure according to the present invention are as follows:

the perimeter part of the absorbent structure is soft and helps keep the skin dry;

the fluff-free absorbent insert gives the absorbent structure high integrity and absorbency characteristics;

the gap between the fluff-free absorbent insert and the cellulose fluff pad gives flexibility and improves wearability;

the absorbent structure has a reduced thickness and is particularly suitable for being included in absorbent sanitary articles for incontinent adults.

Of course, without prejudice to the principle of the invention, the details of construction and the embodiments may be varied, with respect to that described purely by way of non-limiting example, without thereby departing from the scope of the invention as defined by the following claims.

The invention claimed is:

1. A method for producing absorbent structures, comprising:

forming an array of absorbent pads comprising cellulose fluff, wherein each absorbent pad of said array of absorbent pads has at least one through-opening, forming an array of fluff-free absorbent inserts, each fluff-free absorbent insert comprising at least one non-woven layer in which superabsorbent material is incorporated, and arranging said fluff-free absorbent inserts within respective through-openings of said absorbent pads so as to form an array of absorbent structures, each of which comprises an absorbent pad and at least one fluff-free absorbent insert inserted in the through-opening of the respective absorbent pad, wherein the method further comprises:

fixing said array of fluff-free absorbent inserts on a first continuous non-woven web in positions spaced apart from each other along a longitudinal direction, applying said array of absorbent pads on a second continuous non-woven web in positions spaced apart from each other along the longitudinal direction, overlapping said second continuous non-woven web to said first continuous non-woven web, and—at the same time—inserting said fluff-free absorbent inserts into respective through-openings of said absorbent pads and sandwiching said array of absorbent pads and said array of fluff-free absorbent inserts between said first and second continuous non-woven webs.

2. The method of claim 1, comprising fixing said first and second continuous non-woven webs together through the gaps formed between said absorbent pads and respective fluff-free absorbent inserts.

3. A method for producing absorbent structures, comprising:

forming an array of absorbent pads comprising cellulose fluff, wherein each absorbent pad of said array of absorbent pads has at least one through-opening, forming an array of fluff-free absorbent inserts, each fluff-free absorbent insert comprising at least one non-woven layer in which superabsorbent material is incorporated, and arranging said fluff-free absorbent inserts within respective through-openings of said absorbent pads so as to form an array of absorbent structures, each of which comprises an absorbent pad and at least one fluff-free absorbent insert inserted in the through-opening of the respective absorbent pad, wherein the method further comprises:

fixing said array of fluff-free absorbent inserts on a first continuous non-woven web in positions spaced apart from each other along a longitudinal direction, feeding a second continuous non-woven web onto an outer surface of a forming wheel and forming said array of absorbent pads in spaced apart positions along the longitudinal direction on said second continuous non-woven web, overlapping said second continuous non-woven web to said first continuous non-woven web, and—at the same time—inserting said fluff-free absorbent inserts into respective through-openings of said absorbent pads and sandwiching said array of absorbent pads and said array of fluff-free absorbent inserts between said first and second continuous non-woven webs.

* * * * *